United States Patent [19]

Kawanabe et al.

[11] Patent Number: 4,721,084
[45] Date of Patent: Jan. 26, 1988

[54] METHOD FOR CONTROLLING AN OXYGEN CONCENTRATION SENSOR FOR SENSING AN OXYGEN CONCENTRATION IN AN EXHAUST GAS OF AN INTERNAL COMBUSTION ENGINE

[75] Inventors: Tomohiko Kawanabe; Masahiko Asakura; Minoru Muroya; Katsuhiko Kimura; Noritaka Kushida; Hiroshi Hasebe, all of Wako, Japan

[73] Assignee: Honda Giken Kogyo Kabushiki Kaisha, Tokyo, Japan

[21] Appl. No.: 908,854

[22] Filed: Sep. 18, 1986

[30] Foreign Application Priority Data

Sep. 25, 1985 [JP] Japan ............................. 60-211255
Sep. 26, 1985 [JP] Japan ............................. 60-213571

[51] Int. Cl.⁴ ............................................... F02D 5/00
[52] U.S. Cl. ............................ 123/440; 123/489; 204/424
[58] Field of Search ............... 123/440, 486; 60/276; 204/424, 425, 426

[56] References Cited

U.S. PATENT DOCUMENTS

| 4,344,317 | 8/1982 | Hahori | 123/440 |
| 4,354,468 | 10/1982 | Sone | 123/489 |
| 4,359,030 | 11/1982 | Sone | 123/440 |
| 4,365,604 | 12/1982 | Sone | 123/440 |
| 4,548,179 | 10/1985 | Ninomiya | 123/440 |

*Primary Examiner*—Ronald B. Cox
*Attorney, Agent, or Firm*—Pollock, Vande Sande and Priddy

[57] ABSTRACT

Method for controlling an oxygen concentration sensor for sensing an oxygen concentration in an exhaust gas of an internal combustion engine, which sensor includes an oxygen pump element and a heater element, comprises steps for controlling a pump current and a heat current control in response to a result of a detection of engine load. When the engine is operating in a predetermined high load range, the supply of the pump current to the oxygen pump element is stopped, and the heat current to the heater element is reduced when the engine operation in the high load range has continued for more than a predetermined time period. The heater current to the heater element is stopped when the engine load is in a first predetermined load range, and when the engine operation in a second load range which is lighter than the first load range has continued for a predetermined time period.

5 Claims, 11 Drawing Figures

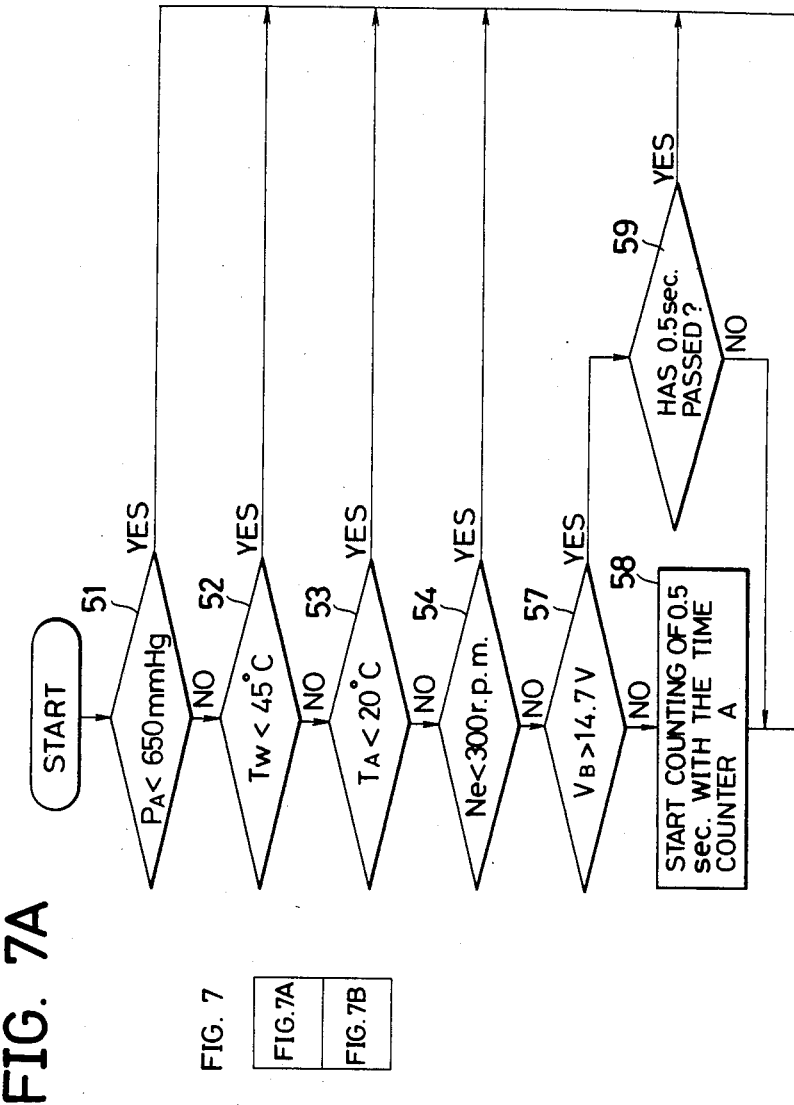

METHOD FOR CONTROLLING AN OXYGEN CONCENTRATION SENSOR FOR SENSING AN OXYGEN CONCENTRATION IN AN EXHAUST GAS OF AN INTERNAL COMBUSTION ENGINE

CROSS REFERENCE TO RELATED APPLICATIONS

Oxygen concentration sensing devices whose structures are similar to those used in the present invention are disclosed in Asakura et al U.S. application Ser. No. 843,951 filed Mar. 25, 1986, Kawanabe et al U.S. application Ser. No. 905,434 filed Sept. 10, 1986, and in Kawanabe et al U.S. application Ser. No. 909,534 and 909,535 filed Sept. 22, 1986, each of which is assigned to the assignee of the instant application.

BACKGROUND OF THE INVENTION

1. Filed of the Invention

The present invention relates to a method for controlling an oxygen concentration sensor for sensing an oxygen concentration in an exhaust gas of an internal combustion engine.

2. Description of Background Information

Air/fuel ratio feedback control systems are becoming generally used for the fuel supply control of an internal combustion engine, and such systems are so constructed that the oxygen concentration in the exhaust gas of the engine is detected by an oxygen concentration sensor and the air/fuel ratio of a mixture to be supplied to the engine is feedback controlled in response to a result of the detection of the oxygen concentration so as to purify the exhaust gas and to improve the fuel economy.

As an example of an oxygen concentration sensor for use in the air/fuel ratio control system of the above mentioned type, there is an oxygen concentration sensor which produces an output signal whose level is proportional to the oxygen concentration in the exhaust gas of the engine in a region in which the air/fuel ratio of mixture to be supplied to the engine is larger than a stoichiometric air/fuel ratio, and the details of such a sensor are described in Japanese Patent Application laid open No. 58-153155. This oxygen concentration sensor includes a sensor element whose general construction includes a pair of flat solid electrolyte members having oxygen ion permeability. These oxygen-ion conductive solid electrolyte members are placed in the exhaust gas of the engine, and two electrodes are provided on the front and back surfaces of both of the solid electrolyte members. In other words, each pair of electrodes sandwich each solid electrolyte member. These two solid electrolyte members, each having a pair of electrodes, are arranged in parallel to each other so as to face each other and to form a gap portion, or in other words, a restricted region between them.

With this arrangement, one of the solid electrolyte members serves as an oxygen pump element and the other of the solid electrolyte members serves as a sensor cell element for sensing an oxygen concentration ratio. In the atmosphere of the exhaust gas, a drive current is supplied across the electrodes of the oxygen pump element in such a manner that the electrode facing the gap portion operates as a negative electrode. By the supply of this current, the oxygen component of the gas in the gap portion is ionized on the surface of the negative electrode of the oxygen pump element. The oxygen ions migrate through the inside of the oxygen pump element to the positive electrode, where the oxygen ions are released from the surface thereof in the form of the oxygen gas.

While this movement of oxygen ions is taking place, the oxygen concentration becomes different for the gas in the gap portion and the gas outside the electrodes of the sensor cell element because of a reduction of the oxygen gas component in the gap portion. Therefore, an electric potential whose magnitude varies substantially linearly in proportion to the oxygen concentration of the gas to be measured is generated across the electrodes of the solid electrolyte member operating as the sensor cell element if the magnitude of the electric current supplied to the oxygen pump element i.e., the pump current, is constant.

By means of this electric potential generated across the electrodes of the sensor cell element, a detection as to whether the air/fuel ratio of mixture supplied to the engine is rich or lean is performed. In the case of the air/fuel ratio control system in which the air/fuel ratio is controlled by the supply of the air intake side secondary air, the secondary air is supplied when the air/fuel ratio is detected to be rich. On the other hand, the supply of the secondary air is stopped when the air/fuel ratio is detected to be lean, and the air/fuel ratio is controlled toward a target air/fuel ratio by the supply and stop of the air intake side secondary air. Further, if the magnitude of the pump current supplied to the oxygen pump element is varied so that the electric potential developing across the electrodes of the sensor cell element becomes constant, the magnitude of the pump current varies substantially in proportion to the oxygen concentration in the exhaust gas, under a condition of a constant temperature. Thus, the oxygen concentration can be detected also by the magnitude of the pump current.

In this type of oxygen concentration sensor, if an excessive current is supplied to the oxygen pump element, it causes the so called blackening phenomenon by which the oxygen ions are removed from the solid electrolyte members. For instance, when zirconium dioxide ($ZrO_2$) is utilized as the solid electrolyte, the oxygen ions $O_2$ are removed from the zirconium dioxide ($ZrO_2$) so that zirconium (Zr) is separated out. As a result of this blackening phenomenon, deterioration of the oxygen pump element takes place rapidly, to cause a debasement of the operation of the oxygen concentration sensor as a whole.

In order to prevent the said phenomenon, the magnitude of the pump current supplied to the oxygen pump element must be controlled below a critical level of the occurrence of the blackening phenomenon.

In this type of oxygen concentration sensor, it is necessary that the temperature of the sensor be sufficiently higher (for example, higher than 650° C.) than an exhaust gas temperature under a steady state operation, in order to obtain a proportional output signal characteristic in which the sensor output signal varies substantially in proportion to the oxygen concentration. To meet this requirement, a heating device which is made up of a heater element is incorporated in the oxygen concentration sensor and a drive current is supplied to the heater element at a time of the detection of the concentration so that heat is generated at the heater element.

Now, operating conditions of an internal combustion engine will be discussed.

When the engine load is high, the air/fuel ratio of the mixture supplied to the engine may be controlled to a rich side by the operation of a fuel increment control device of the engine such as an acceleration pump of the carburetor or a power valve. The critical value of the pump current for the occurrence of the blackening phenomenon reduces as the air/fuel ratio becomes richer. Therefore, the blackening phenomenon is likely to occur under this condition. In order to prevent the occurrence of the blackening phenomenon, the air fuel ratio of the mixture to be supplied to the engine can be controlled to the lean side while the level of the pump current is limited below the critical level of the occurrence of the blackening phenomenon. However, it was generally not possible to prevent the occurrence of the blackening phenomenon completely because there inevitably is a lag between the time that control of the air/fuel ratio of the mixture commences and the time at which a result of the air/fuel ratio control appears as a change in the oxygen concentration in the exhaust gas.

On the other hand, when the engine load is high, the amount of the mixture taken into the engine becomes also high, and this results in an increase of the combustion temperature. Under such a condition, the temperature of the exhaust gas also rises to a level higher than the temperature of the heater element. Because of this, there is a possibility of rapid deterioration of the heater element. The assignee of the present application has proposed a control method in which the supply of the heater current to the heater element is stopped so as to prevent a rapid deterioration of the heater element when the engine load is high. However, in the case of such a control method, a time period is required for the resumption of the operation of the pump element and the sensor cell element if the supply of the heater current to the heater element is always stopped under a high load condition. Therefore, an accurate sensing of the air/fuel ratio using the output signal level of the oxygen concentration sensor is not possible even if the condition of the feedback control is satisfied.

Further, if the high load operation of the engine is detected by means of the rotational speed of the engine, the supply of the heater current to the heater element is enabled or stopped repeatedly when the engine speed is at around a reference speed for the detection of the high load operation. Above all, the repetition of the supply or the stop of the heater current may shorten the life of the heater element. Further, under such a condition, the output signal level of the oxygen concentration sensor fluctuates even though the air/fuel ratio is constant, because of the change in the calorific power of the heater element. For avoiding this problem, it is conceivable to set the reference speed for detecting the high load operation at a low level. However, such a method is not desirable because the feedback control range of the air/fuel ratio is reduced to lower the performance of the emission control.

Moreover, once the supply of the heater current is stopped, it requires a time period after a resumption of the supply of the heater current until the oxygen pump element and the sensor cell elements are activated again. Therefore, it is not possible to detect the air/fuel ratio accurately from the output signal level of the oxygen concentration sensor when the engine speed is reduced below the reference speed, to satisfy the condition of the air/fuel ratio feedback control. Because of the reasons described above, repetition of the supply and stopping of the heater current to the heater element leads to a reduction of the range of the air/fuel ratio feedback control.

OBJECTS AND SUMMARY OF THE INVENTION

An object of the present invention is therefore to provide a method for controlling an oxygen concentration sensor by which the occurrence of the blackening phenomenon under a high load condition is prevented and an accurate detection of the air/fuel ratio is enabled in a short time after the restarting the supply of the heater current of the heater element.

Another object of the present invention is to provide a method for controlling the oxygen concentration sensor by which the heater element of the oxygen concentration sensor is well protected during the high load operation of the engine while the efficiency of the emission control operation is improved.

According to the present invention, a method for controlling an oxygen concentration sensor is characterized in that the current supply to the oxygen pump element is stopped when the engine load is in a predetermined high load range, and the supply of the current to the heater element is reduced or stopped when an operating condition of the engine in which the engine load is in the predetermined high load range has continued for a predetermined time period.

According to another aspect of the present invention, the supply of the heater current to the heater element is stopped when the engine load is in a first load range, and when a condition in which the engine load is in a second load range which is lighter than the first load range has continued for more than a predetermined time period.

BRIEF DESCRIPTION OF THE DRAWINGS

FIGS. 7A and 7B, when combined, are a flowchart showing steps of the control method according to the present invention;

FIG. 7 is a diagram showing the manner in which FIGS. 7A and 7B are combined;

DETAILED DESCRIPTION OF THE PREFERRED EMBODIMENT

Figure 1:
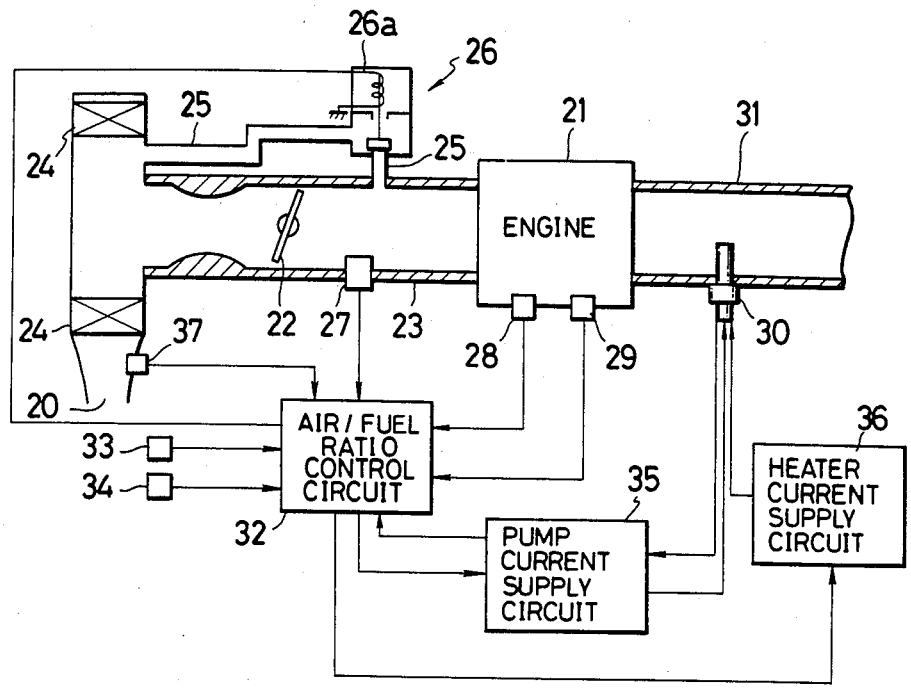
FIG. 1 is a block diagram showing an example of the air/fuel ratio control system in which a control method according to the present invention is applied.

FIG. 1 exemplarily shows an air/fuel ratio control system for an automotive internal combustion engine in which the method for controlling an oxygen concentration sensor according to the present invention is adopted.

As shown, an internal combustion engine generally denoted by a reference numeral 21 has a throttle valve 22 and an intake manifold 23. The intake manifold 23 which is downstream of throttle valve 22 communicates with the inside of an air cleaner 24, near an air outlet port thereof, via an air intake side secondary air supply passage 25. An open-close solenoid valve 26 is provided in the secondary air supply passage 25, and arranged to open when a drive current is supplied to its solenoid 26a.

The intake manifold 23 is provided with an absolute pressure sensor 27 which produces an output signal whose level is responsive to an absolute pressure in the intake manifold 23. In addition to this absolute pressure sensor 27, the air/fuel ratio control system includes various sensors such as a rotational speed sensor 28 which produces an output signal whose level is responsive to a rotation of a crankshaft (not shown) of the engine 21, and a cooling water temperature sensor 29 for producing an output signal whose level is responsive to the temperature of the cooling water of the engine 21. The reference numeral 37 denotes an intake air temperature sensor provided on the air cleaner 24 near its air inlet port 20, and the reference numeral 30 denotes an oxygen concentration sensor which produces an output signal which varies substantially in proportion to the oxygen concentration in the exhaust gas, and mounted on an exhaust manifold 31 of the engine 21.

The open-close solenoid valve 26, the absolute pressure sensor 27, the rotational speed sensor 28, the cooling water temperature sensor 29 and the intake air temperature sensor 37 are connected to an air/fuel ratio control circuit 32 in which a microcomputer is provided. The air/fuel ratio control circuit 32 further receives an output signal of an atmospheric pressure sensor 33 whose level is responsive to atmospheric pressure. An ignition switch 34 is also connected to this air/fuel ratio control circuit 32 so that an output voltage of a battery (not shown) mounted on the vehicle is supplied thereto.

The oxygen concentration sensing part includes a pump current supply circuit 35 which supplies a pump current to the oxygen pump element of the oxygen concentration sensor 30 and a heater current supply circuit 36 for supplying a heater current to the heater element of the oxygen concentration sensor 30. The pump current generating circuit 35 and the heater current supply circuit 36 are also connected to the air/fuel ratio control circuit 32.

Figure 2:
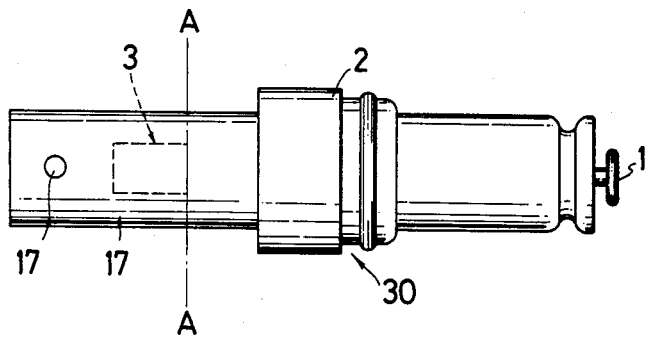
FIG. 2 is a side view of an oxygen concentration sensor utilized in the air/fuel ratio control system shown in FIG. 1.

As shown in FIG. 2, the oxygen concentration sensor 30 includes a housing 2 having a lead wire introducing hole 1 at an extremity thereof. At the other extremity of the housing 2, an oxygen concentration sensing element 3 is mounted. The oxygen concentration sensing element 3 is surrounded by a protection cover 17 which is formed into a cylinder and connected to the housing at an end portion thereof. The protection cover 17 is provided with a plurality of exhaust gas introduction holes 17a which are equally spaced around the circumference of the cover. Four exhaust gas introduction holes 17a are provided in this example. In addition, a part of the oxygen concentration sensor 30 illustrated on the left side of the line A—A of FIG. 2 is introduced into the exhaust manifold 31 when the sensor 30 is mounted for operation.

Figure 3:
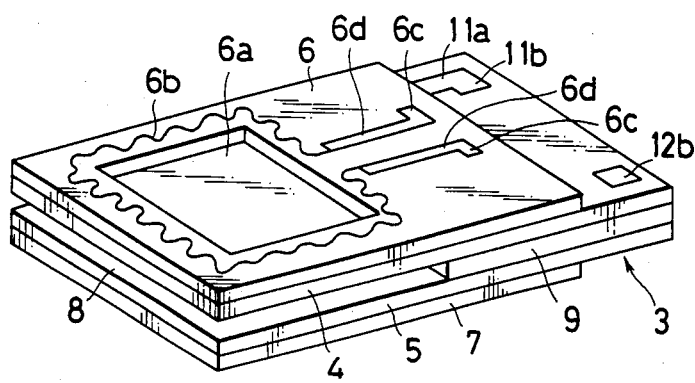
FIG. 3 is a perspective view of an oxygen concentration sensing element provided in the oxygen concentration sensor shown in FIG. 2.
Figure 4:
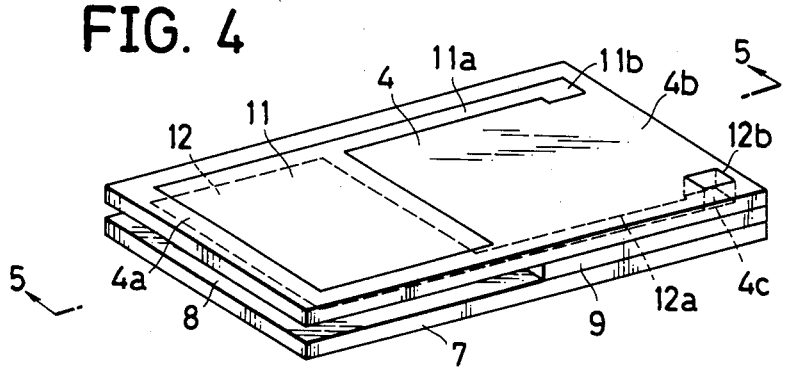
FIG. 4 is a perspective view corresponding to FIG. 3, showing the oxygen concentration sensing element from which heater elements 6 and 7 shown in FIG. 3 are removed.
Figure 5:
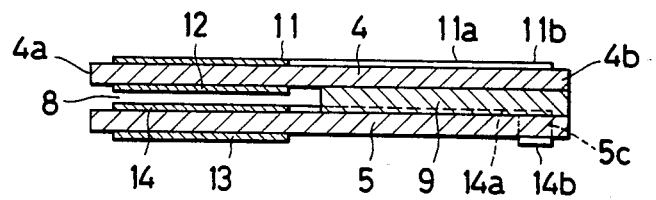
FIG. 5 is a vertical cross-sectional view taken on the plane of the lines 5—5 of FIG. 4, illustrating an internal construction of the oxygen concentration sensing element.

As illustrated in FIG. 3, the oxygen concentration detection element 3 comprises a pair of flat elongated elements 4 and 5 and a pair of flat heater elements 6 and 7 respectively provided on the outer sides of the flat elongated elements 4 and 5. As clearly shown in FIGS. 4 and 5, the flat elongated elements 4 and 5 are arranged in parallel with each other, so that main surfaces of both elements 4 and 5 face each other. A gap portion 8 is formed between end portions of the flat elongated elements 4 and 5 which are connected together by means of a spacer 9 at the other end portions (second end portions) thereof. One of the flat elongated elements 4 and 5, (element 4) is an oxygen pump element whose main part is made of a sinter of an oxygen-ion conductive solid electrolyte. The oxygen pump element 4 is, at corresponding positions of both surfaces of an end portion 4a thereof, provided with a pair of square electrode layers 11 and 12 made of a porous heat resisting metal. One of the square electrode layers 11 and 12 (the electrode layer 11) is connected, at a corner thereof, to a lead wire 11a which is made of a heat resisting metal and linearly extends to the second end portion 4b of the oxygen pump element 4. Similarly, the other one of the square electrode layers 11 and 12 (the electrode layer 12) is connected, at a corner thereof which is away from the connection point between the square electrode layer 11 and the lead wire 11a, to a lead wire 12a also made of the heat resisting metal and linearly extending to the second end portion 4b of the oxygen pump element 4. The lead wire 12a is connected to a terminal part 12b located on the other side, after running through a through hole 4c which passes between the front and back faces of the oxygen pump element 4. The lead wire 11a is connected to a terminal part 11b also formed on the second end portion 4a. In short, the terminal parts 11b and 12b respectively of the lead wires 11a and 12a are provided on one of the main surfaces of the oxygen pump element 4.

The other one of the flat elongated elements (the element 5) is a sensor cell element for sensing an oxygen concentration ratio, and is also made of the sinter of the oxygen-ion conductive solid electrolyte. This sensor cell element 5 is constructed in the same manner as the oxygen pump element 4, and is provided, on both of the front and back surfaces thereof, with square electrode layers 13 and 14, and lead wires 13a and 14a. Terminal parts 13b and 14b are provided on one of the main surfaces in which the electrode layer 13 is formed. In addition, the lead wire 14a and the terminal part 14b are connected to each other by means of a through hole 5c.

Typical examples of the above explained oxygen-ion conductive solid electrolyte member for the elements 4 and 5 are solid solution of zirconia with yttria or calcia. However, other solid solutions of cerium dioxide, thorium dioxide, or hafnium dioxide may be also used. As the electrode layers 11 through 14, the lead wires 11a through 14a, the terminal parts 11b through 14b, platinum (Pt), Ruthenium (Ru), and Palladium (Pd) may be used. In production, the above mentioned metal is applied to form a coating by a suitable method such as flame spraying, chemical plating, or evaporation.

Next, the flat heater elements 6 and 7 illustrated in FIG. 3 will be explained.

The main body of the heater elements 6 and 7 is a rectangular plate made of an inorganic insulating material such as alumina or spinel. The lengthwise size of the heater elements 6 and 7 is slightly smaller than that of the flat elongated elements 4 and 5. An end portion of the heater element 6, an opening portion 6a is provided in registration in size and position with the electrode layer 11 on the oxygen pump element 4. The heater element 6 includes a wavelike heater wire 6b provided around the opening portion 6a. The heater wire 6b is electrically connected to a terminal part 6c which is formed in the other end portion of the heater element 6, through a lead wire 6d. The heater wire 6b, the terminal part 6c, and the lead wire 6d are made of a heat resisting metal such as platinum (Pt). Although not illustrated in the drawings, the other heater element 7 is also provided with an opening, a heater wire (which will be denoted by 7b in the following description) and a lead wire correspondingly to the heater element 6.

An oxygen concentration detection operation of the oxygen concentration sensor 30 having the above explained configuration will be discussed hereinafter.

A pump current is supplied across the electrode layers 11 and 12 of the oxygen pump element 4 from the pump current supply circuit 35 so that the electrode layer 11 which is located on the outer side of the oxygen pump element 4 operates as a positive electrode. By the supply of the pump current, oxygen ions migrate, from the inner electrode layer 12 to the outer electrode layer 11, through the solid electrolyte member of the oxygen pump element 4. As a result, oxygen in the gap portion 8 between the oxygen pump element 4 and the sensor cell element 5 is pumped toward the outside of the oxygen pump element.

When the oxygen is pumped out from the gap portion 8 as explained above, the oxygen concentration becomes different for the gas outside of the sensor cell element 5, i.e. the exhaust gas, and the gas in the gap portion 8. This difference of the oxygen concentration causes an electric potential to be generated across the electrode layers 13 and 14 of the sensor cell element 5. This electric potential will reach a constant level when the amount of oxygen which flows into the gap portion 8 freely from openings of three directions in the cover 17 of the sensor and the amount of oxygen pumped out from the gap portion 8 by the operation of the oxygen pump element 4 have attained an equilibrium.

The thus generated electric potential is supplied to the pump current supply circuit 35 by which a pump current value $I_p$ is varied so that the electric potential generated across the electrodes of the sensor cell element 5 is maintained at a predetermined constant level. Therefore, under a condition of a constant temperature, the pump current value $I_p$ becomes proportional to the oxygen concentration in the exhaust gas.

In the air/fuel ratio control circuit 32, a detection as to whether the air/fuel ratio of mixture supplied to the engine 21 is richer than a target air/fuel ratio or leaner than the target air/fuel ratio is performed using the pump current value $I_p$ supplied from the pump current supply circuit 35 to the oxygen pump element 4. Specifically, the air/fuel ratio of mixture is detected to be rich when the pump current value $I_p$ is below a reference level corresponding to the target air/fuel ratio. On the other hand, the air/fuel ratio is detected to be lean when the pump current value $I_p$ is above the reference level.

By controlling the opening and closing of the open-close solenoid valve 26 in response to a result of the detection of the air/fuel ratio of the mixture explained above, the amount of the air intake side secondary air supplied to the intake manifold 23 is controlled. The air/fuel ratio of the mixture is feedback controlled toward the target air/fuel ratio in this way.

The heater elements 6 and 7 are respectively supplied with a heater current from the heater current supply circuit 36 across the terminal parts 6c and 7c. The heater current flows through the lead wires 6d (7d) and the heater wire 6a (7a) which in turn heats the oxygen concentration detection element 3 as a whole.

Figure 6:
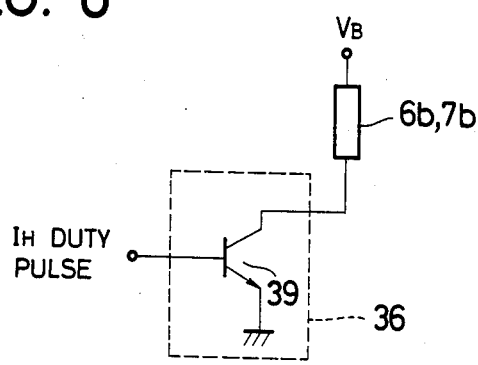
FIG. 6 is a circuit diagram of a heater current supply circuit used in the system of FIG. 1.

The supply of the heater current from the heater current supply circuit 36 is duty-ratio controlled by an operation of the air/fuel ratio control circuit 32. The air/fuel ratio control circuit 32 provides $I_H$ duty pulses which indicate a heater current value $I_H$ to the heater current supply circuit 36. As illustrated in FIG. 6, the heater current supply circuit 36 receives the $I_H$ duty pulses, and comprises a switching transistor 39 which turns on to supply a battery voltage $V_B$ to the heater wire 6b (7b) upon receipt of each pulse of the $I_H$ duty pulses.

Figure 7B:
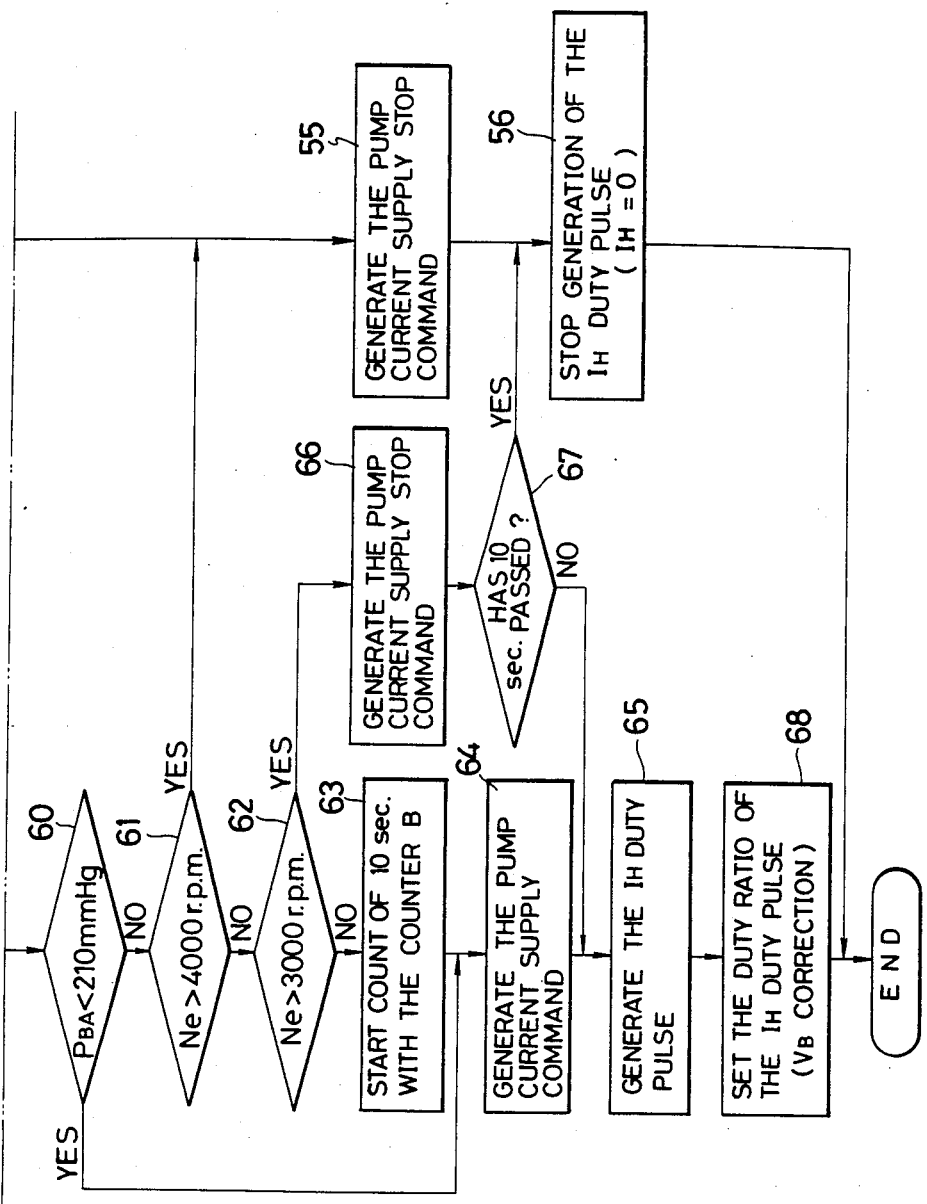

Referring to the flowchart of FIG. 7, steps of the method for controlling the oxygen concentration sensor according to the present invention which is performed by the air/fuel ratio control circuit 32 will be explained hereinafter.

The air/fuel ratio control circuit 32 detects whether or not the atmospheric pressure $P_A$ is lower than 650 mmHg, at a step 51. Similarly, at steps 52 through 54, the air/fuel ratio control circuit 32 detects whether or not the cooling water temperature Tw is lower than 45° C., whether or not the intake air temperature $T_A$ is lower than 20° C., and whether or not the engine rotational speed Ne is lower than 300 r.p.m. If $P_A<650$ mmHg, it means that the vehicle is running at a place of high altitudes. If Tw<45° C., it means that the cooling water is not sufficiently warmed up. If $T_A<20°$ C., it means that the intake air temperature is low. Further, if Ne<300 r.p.m., it means that the engine is cranking. Under any of these conditions, it is necessary to stop the feedback control of the air/fuel ratio toward a value in the lean region. Therefore, the air/fuel ratio control circuit 32 supplies, at a step 55, a pump current supply stop command to the pump current supply circuit 35. At the same time, it controls the duty ratio of the $I_H$ duty pulses to 0% so that the supply of the heater current is stopped ($I_H=0$). In other words, the air/fuel ratio control circuit 32 stops the supply of the $I_H$ duty pulses to the heater current supply circuit 36 at a step 56.

On the other hand, when all of the conditions of, $P_A \geq 650$ mmHg, Tw$\geq 45°$ C., TA$\geq 20°$ C., and Ne$\geq 300$ r.p.m. are satisfied, the air/fuel ratio control circuit 32 detects whether or not the battery voltage $V_B$ is higher than 14.7 V at a step 57. If $V_B \leq 14.7$ V, the air/fuel ratio control circuit 32 sets a time count value of 0.5 sec, in an internal time counter (not shown), and starts a down counting at a step 58. If $V_B>14.7$ V, it means that the battery voltage $V_B$ is excessively high. In this case, the air/fuel ratio control circuit 32 detects whether or not the high voltage state has continued for more than 0.5 second, using a count value of the time counter A at a step 59. If the high voltage state has continued for more than 0.5 second, an excessive electric power is supplied to the heater elements 6 and 7, and the heater elements 6 and 7 may be destroyed by heat. Therefore, the air/fuel ratio control circuit executes the operations of the steps 55 and 56 so as to stop the supply of the heater current.

When the high voltage state of the battery has not continued for 0.5 second, or after the operation of the step 58, whether or not the intake air pressure $P_{BA}$ is smaller than 210 mmHg is detected at a step 60. If $P_{BA} \geq 210$ mmHg, the air/fuel ratio control circuit 32 then detects whether or not the engine speed Ne is higher than 4000 r.p.m. at a step 61. If Ne>4000 r.p.m., the amount of intake air is increased to raise the exhaust gas temperature higher than a temperature level obtained by heat generated by the heater elements 6 and 7. Therefore, under this condition, the air/fuel ratio control circuit 32 executes the steps 55 and 56 to stop the supply of the heater current so as to protect the heater elements 6 and 7 from over heating. When Ne≦4000 r.p.m., whether or not the engine speed is higher than 3000 r.p.m. is detected at a step 62. If Ne≦3000 r.p.m., the air/fuel ratio control circuit 32 sets a count time of 10 seconds in an internal time counter B (not shown), and starts the down counting at a step 63. Subsequently, the air/fuel ratio control circuit 32 supplies the pump current supply command to the pump current supply circuit 35 at a step 64, and supplies the duty pulses having a preset value ($I_H \neq 0$) for the detection of the oxygen concentration, to the heater current supply circuit 36 at a step 65.

If, at the step 60, it is detected that $P_{BA} < 210$ r.p.m., it means that the engine load is light, and the operation of the step 64 is immediately executed. If Ne>3000 r.p.m., i.e. if 4000 r.p.m.≧Ne>3000 r.p.m., the air/fuel ratio control circuit 32 provides the pump current supply stop command to the pump current supply circuit 35 at a step 66. At the same time, whether or not this state of the rotational speed has continued for more than 10 seconds is detected by using a count value of the time counter B, at a step 67. If this state of the rotational speed in the predetermined range (4000 r.p.m.≧Ne>3000 r.p.m.) has continued for more than 10 seconds, the operation of the step 56 is executed to stop the supply of the heater current. If, on the other hand, the state of the rotational speed in the predetermined range, has not continued for more than 10 seconds, the operation of the step 65 is executed.

Figure 8:
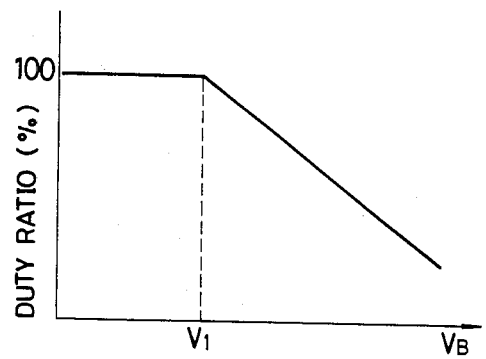
FIG. 8 is a diagram showing a duty ratio setting characteristic of an $I_H$ duty pulse used in the control method according to the present invention.

After the execution of the operation of the step 65, the air/fuel ratio control circuit 32 effects a correction of the heater current value $I_H$ in response to the battery voltage $V_B$ at a step 68. This correction is performed, assuming that the standard value of the battery voltage is expressed by Vr, by setting the duty ratio $T_{HOE}$ of the $I_H$ duty pulses of the air/fuel ratio control circuit 32 at a level, for example, determined by a formula of 100-K($V_B$-Vr), where K is a constant and this formula is used only when $V_B$>Vr. As shown in FIG. 8, the duty ratio $T_{OHE}$ of the $I_H$ duty pulses determined in this way becomes 100% when the battery voltage is low, and decreases as the battery voltage $V_B$ goes up, under a condition that the battery voltage is higher than the standard value of the battery voltage Vr.

The heater current value $I_H$ is controlled by the air/fuel ratio control circuit 32 by repeatedly executing the above explained steps.

Figure 9:
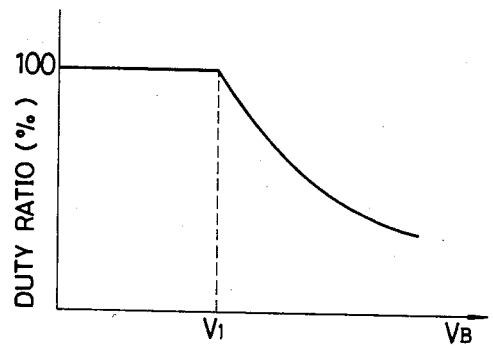
FIG. 9 is a diagram similar to FIG. 8, showing another example of the duty ratio setting characteristic.

Additionally, it is possible to modify the system operation so that the operation of the step 64 is inhibited when the pump current is being supplied. Similarly, it is possible to modify the system operation such that the operation of the step 65 is inhibited when the heater current is being supplied. Also, it is possible to set the duty ratio $T_{OHE}$ of the IH duty pulse provided by the air/fuel ratio control circuit 32 at the step 68 in accordance with a formula of (Vr/$V_B$)×100. The variaion of the duty ratio $T_{OHE}$ of the $I_H$ duty pulses in this case is shown in the curve of FIG. 9. As shown, the variation of the duty ratio TOHE is generally the same as that shown in FIG. 8.

In the preferred embodiment explained so far, the air/fuel ratio is detected by using the magnitude of the pump current as the output signal of the oxygen concentration sensor. However, it is also possible to so arrange the system that the magnitude of the pump current is controlled at a predetermined level. In that case, the level of the electric potential developed across the electrodes of the sensor cell element can be utilized as the output signal of the oxygen concentration sensor. It is to be noted that, also in that case, the manner of control of the oxygen concentration sensor is substantially the same as in the above explained embodiment.

Further, in the above explained embodiment, the engine load is detected by using the engine rotational speed. However, the engine load can be also detected by using another engine parameter such as the intake air absolute pressure, the opening degree of the throttle valve, and so on.

It will be appreciated from the foregoing, in the method for controlling the oxygen concentration sensor according to the present invention, the supply of the pump current to the oxygen pump element is stopped when the engine operation is in a predetermined high load range. Thus, the occurrence of the blackening phenomenon is avoided and the rapid deterioration of the oxygen pump element is prevented. Moreover, the supply of the heater current to the heater element is stopped or the magnitude of the heater current is reduced when engine operation in the high load range has continued for a predetermined time period. With this feature, the temperature of the heater element becomes more stable than in the conventional control method in which the heater current to the heater element is stopped continuously when the engine operation is in a predetermined high load range every time that the engine operation is of the same operational pattern. This is because the number of reductions or stops of the current supply to the heater element is reduced as compared with the conventional arrangement. Therefore, an accurate detection of the air/fuel ratio by means of an output signal level of the oxygen concentration sensor is enabled soon after the resumption of the current supply to the heater element.

Moreover, according to the method for controlling the oxygen concentration sensor of the present invention, the supply of the heater current to the heater element is stopped when the engine load is in the first load range. The supply of the heater current is also stopped when the condition in which the engine load is in a second load range which is lighter than the first load range has continued for more than the predetermined time period. With this feature, a rapid overheating of the heater element is prevented by stopping the supply of the heater current when the exhaust gas temperature is higher than the temperature attained by the operation of the heater element under the high load condition of the engine. Thus, damage to the heater element or a rapid deterioration of the heater element is prevented.

Further, a frequent repetition of the supply and stop of the heater current to the heater element is prevented so that the calorific power of the heater element is stabilized and the adverse effects on the output signal of the oxygen concentration sensor is prevented. As will be appreciated from the foregoing, the efficiency of the emission control can be very much improved by an air/fuel ratio control in which the method for controlling the oxygen concentration sensor according to the present invention is adopted.

What is claimed is:

1. A method for controlling an oxygen concentration sensor used in an air/fuel ratio control system for an internal combustion engine, said oxygen concentration sensor including: an oxygen concentration sensing unit disposed in an exhaust passage of said internal combustion engine, said sensing unit including an oxygen pump element and a sensor cell element which define a diffusion restricted region therebetween, each of said elements including a solid electrolyte member having oxygen ion permeability and a pair of electrodes sandwiching said electrolyte member therebetween;

pump current supply means for supplying a pump current across the electrodes of said oxygen pump element so as to maintain a voltage generated across the electrodes of said sensor cell element thereby causing said sensing unit to monitor a magnitude of said pump current which is substantially in proportion to the oxygen concentration in the exhaust gas; a heater element for heating said oxygen pump element in accordance with a magnitude of a current supplied thereto; and a source of heater current for supplying a heater current to the heater element, comprising:

a load detection step for detecting a magnitude of an engine load;

a pump current control step for normally supplying said pump current to said oxygen pump element, and stopping the supply of the pump current to said oxygen pump element when it is detected by said load detection step that the engine is operating in a predetermined high load range; and a heat current control step for supplying said heat current to said heater element, and reducing the magnitude of said heater current to said heater element or stopping the supply of the pump current when it is detected by said load detection step that the engine is operating in said high load range at least for a predetermined time period.

2. A method for controlling an oxygen concentration sensor used in an air/fuel ratio control system of an internal combustion engine, said oxygen concentration sensor including an oxygen concentration sensing unit, disposed in an exhaust passage of said internal combustion engine, which includes an oxygen pump element and a sensor cell element which define a diffusion restricted region therebetween, and each of said elements including a solid electrolyte member having oxygen ion permeability and a pair of electrodes sandwiching said electrolyte member therebetween; pump current supply means for supplying a pump current across the electrodes of said oxygen pump element so as to maintain a voltage generated across the electrodes of said sensor cell element thereby causing said sensing unit to monitor a magnitude of said pump current which is substantially in proportion to the oxygen concentration in the exhaust gas; a heater element for heating said oxygen pump element in accordance with a magnitude of a current supplied thereto; and a source of heater current for supplying a heater current to the heater element, said method comprising:

a load detecting step for detecting a magnitude of an engine load; and a heater current control step for normally supplying said heater current to said heater element, and stopping the supply of said heater current when it is detected by said load detecting step that said engine is operating in a predetermined first load range, and when it is detected that the engine operation has continued in a predetermined second load range lighter than said first load range for more than a predetermined time period.

3. A method as recited in claim 1, wherein said magnitude of said heater current to said heater element is reduced to zero when it is detected by said load detection step that the engine is operating in said high load range at least for a predetermined time period.

4. A method as recited in claim 1, wherein an engine rotational speed is detected by said load detection step, and said high load range is a rotational speed range in which the engine rotational speed is higher than a predetermined value.

5. A method as recited in claim 2, wherein a rotational speed of the engine is detected by said load detection step, said first load range is a range in which the rotational speed of the engine is higher than a predetermined first rotational speed value, and said second load range is a range in which the rotational speed of the engine is equal to or lower than said first rotational speed value, and higher than a second rotational speed value which is lower than said first rotational speed value.

* * * * *